Figure 1A:
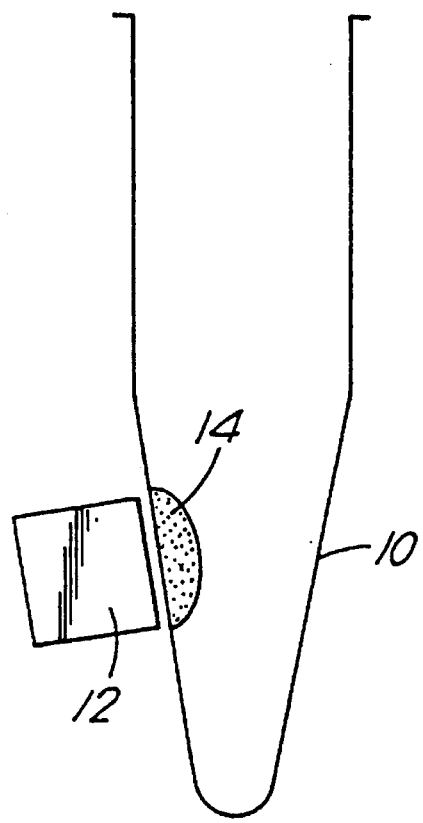

United States Patent [19]

Howe et al.

[11] Patent Number: 5,458,785
[45] Date of Patent: Oct. 17, 1995

[54] MAGNETIC SEPARATION METHOD

[75] Inventors: Roland P. Howe, Calvert; Michael A. Reeve, Henley-on-Thames, both of United Kingdom; Daniel Bischof, Jona, Switzerland

[73] Assignee: Amersham International plc, United Kingdom

[21] Appl. No.: 125,811

[22] Filed: Sep. 24, 1993

[30] Foreign Application Priority Data

Sep. 24, 1992 [EP] European Pat. Off. ............. 92308727

[51] Int. Cl.⁶ .................................................. B01D 35/06
[52] U.S. Cl. ...................... 210/695; 210/222; 436/178; 436/526; 335/304; 335/306
[58] Field of Search ..................... 210/222, 695; 422/100, 101; 436/177, 178, 526; 335/302, 304, 306

[56] References Cited

U.S. PATENT DOCUMENTS 3,981,776  9/1976  Saxholm ................................ 436/526
4,793,973  12/1988  Ringrose .............................. 210/222

FOREIGN PATENT DOCUMENTS

| 479448 | 4/1992 | European Pat. Off. . |
| 3925093 | 1/1991 | Germany . |
| 9014891 | 12/1990 | WIPO . |
| 91-09308 | 6/1991 | WIPO . |
| WO91/12079 | 8/1991 | WIPO . |
| 92-05443 | 4/1992 | WIPO . |

OTHER PUBLICATIONS

Kimura et al., Industrial & Engineering Chemistry Research, 28(6) 803–808 (1989).

Primary Examiner—Matthew O. Savage
Attorney, Agent, or Firm—Wenderoth, Lind & Ponack

[57] ABSTRACT

Biological assay systems often involve suspending magnetically attractable particles in a liquid, and later bringing down the particles from suspension and separating the formed pellet from the supernatant liquid. The invention provides magnetic systems for this purpose, shaped to form an annular or part-annular pellet close to the bottom of the vessel. The systems are suitable for automation.

9 Claims, 4 Drawing Sheets

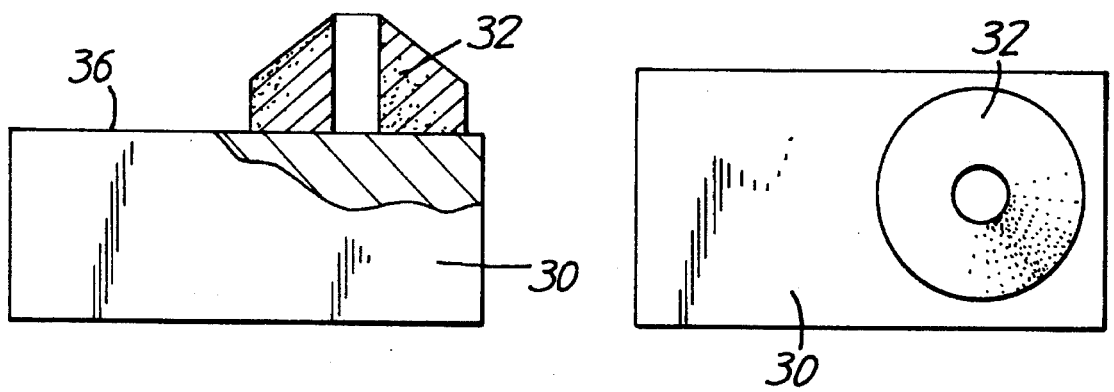
FIG. 3A
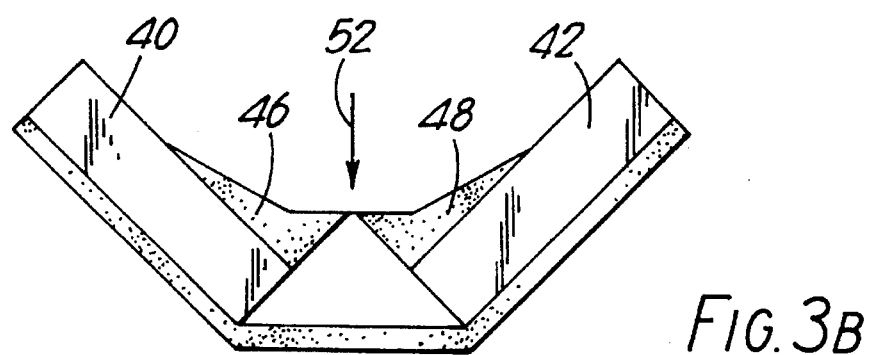
FIG. 3B
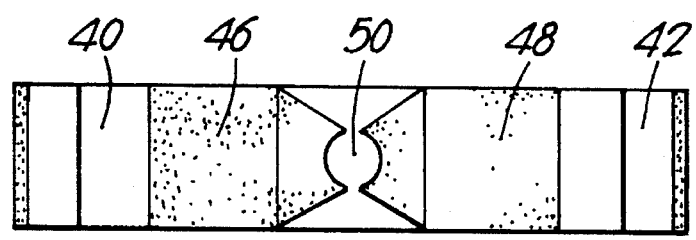

MAGNETIC SEPARATION METHOD

INTRODUCTION

Magnetic separation techniques are increasingly used for the purification or quantification of biological molecules. Techniques that use magnetically attractable particles for the separation of specific molecules from a liquid are well documented in biochemical, biomedical and molecular biology research.

These techniques involve the suspension of magnetically attractable particles in a liquid that contains molecules of interest in an impure or dilute form. The molecules are then captured by the magnetic particles by virtue of specific, or non-specific interactions. Application of a magnetic field to the vessel containing the particles will cause them to migrate towards the source of the field, thus concentrating them at the wall of the vessel. With the magnetic field still applied the remaining liquid (the supernatant) can be discarded by pouring it off or by using a pipetting device, leaving the 'pellet' of particles intact. Additional liquid can then be added and the magnetic field removed, thus allowing the particles to be resuspended. If the interaction between particle and molecule of interest is disrupted at this stage, the purified/concentrated molecules can be recovered by reapplying the field and removing and retaining the supernatant.

The sequence of manipulations consisting of magnetic separation, supernatant removal, addition of liquid and pellet resuspension is common to most of the techniques that utilize magnetically attractable particles. This process may be repeated a number of times during a typical technique, as there may be an initial capture step, followed by one or more treatment or washing steps and a final recovery step.

Magnetic separation techniques are used routinely in many manually operated procedures, but the principle also has great potential for use in automated or robotic systems. However, the apparatus and manipulations currently used are not amenable to simple and reliable automation for the reasons described in section 2).

This invention, described in section 3), provides systems of apparatus and procedures that enable efficient and relatively simple automation of magnetic separation techniques. The same systems may also be used in manual techniques.

CONVENTIONAL SYSTEMS.

The apparatus typically used to carry out this process consists of a rack into which one or more small volume vessels can be inserted (typically small centrifuge tubes or multi-well plates). An arrangement of dipole magnets allows the magnetic particles to be drawn to the side or bottom of each tube or well. FIG. 1 comprises sectional side elevations A and B which illustrate the principles employed by the two most commonly used types of apparatus.

Application and removal of the magnetic field in manual systems is usually achieved by inserting the tubes/plates into the apparatus and then removing them. Automated systems could potentially use mechanically actuated permanent magnets or switched electromagnets, although no such systems are yet commercially available.

Figure 1B:
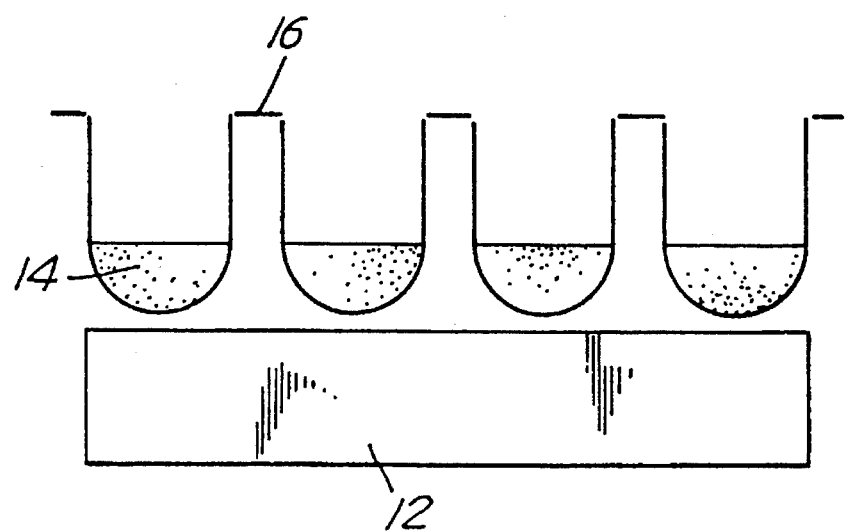

In FIG. 1A, a single vessel 10, commonly an Eppendorf tube, has been brought into proximity with a magnet 12, whereby a pellet 14 comprising magnetically attractable particles has been formed. In FIG. 1B, a microtitre plate 16 has been brought into proximity with a magnet 12, and a pellet 14 comprising magnetically attractable particles has formed in the bottom of each vessel of the plate.

System A uses a magnet which draws the magnetically attractable particles to the side of the vessel, leaving the bottom clear. This enables liquid to drain from the pellet during supernatant removal and be efficiently removed manually or robotically using a pipetting device inserted to the full depth of the vessel. One drawback in automated systems occurs when the pellet must be resuspended in a small volume of liquid, as is usually necessary in order to achieve the maximum possible concentration of the molecule of interest. The pellet adhering to the side of the tube must be washed off by repeatedly drawing up liquid from the bottom of the tube and expelling it at the side of the vessel above the pellet until all the material is resuspended. This process requires accurate control of pipette movement in three dimensions and visual feedback to ensure resuspension, which can not be achieved in a simple robotic system.

It might appear possible to position the magnet 12 nearer the bottom end of the tube 10 so as to form the pellet 14 at a position where it would be immersed by the re-suspending liquid. This is often unsatisfactory in practice, because the magnetic field is then too weak to rapidly draw down magnetically attractable particles that were initially near the surface of the liquid suspension. Also the pellet will still occupy a fairly large vertical segment of the tube, so requiring a large volume of the re-suspending liquid to immerse it.

In EPA 479,448 and also EPA 317,286 are described magnet systems designed to draw down an annular or part-annular pellet of magnetizable beads. This arrangement simplifies the removal of supernatant liquid by a pipette, but the efficient re-suspension of the magnetizable beads remains problematic.

System B illustrates apparatus in which the particles are drawn to the bottom of the vessel. In this case complete resuspension can be easily achieved in manual or automated systems with a simple pipetting device inserted to the full depth of the vessel. Supernatant removal can be performed by either inverting the apparatus or inserting a pipette as close as possible to the pellet. Neither of these methods is very suitable for automation. Inversion is inelegant and complex to achieve in an automated system and is also unacceptable if hazardous materials are involved. Pipetting does not drain the pellet well and again requires visual feedback to position the pipette accurately.

THE INVENTION

This invention is based on the idea of using a magnet system which operates in two modes depending on the relative positions of the vessel and the magnet:

—an annular separation position, and

—a pull-down separation position.

A preferred magnet system, for use in the method and apparatus aspects of the invention, is described and forms a further aspect of the invention.

In the annular separation position, the magnet system is arranged to attract the magnetically attractable particles into an annular (ring) or part-annular pellet near the bottom end of the vessel. This conformation enables a pipette, robotic or manual, to be inserted through the center of the annulus to the bottom of the vessel to fully drain the pellet and remove the supernatant. The top half of FIG. 2 of the accompanying drawings, entitled A, annular separation, contains schematic sectional side elevation and plan views of tube 20 with an annular pellet 22 positioned near the bottom end 24.

After removal of the magnetic field, the pellet can be resuspended by adding liquid to the level of the upper edge of the annulus 22 and drawing the liquid into the pipette and expelling it again a number of times. This resuspension can be made more efficient and reliable by two modifications: a)

a) After adding the resuspension liquid, drawing the annular pellet down to the bottom of the vessel. This is shown in the lower part of FIG. 2, B, pull-down separation, which comprises sectional side elevation and plan views of the same tube with a pellet 26 at the bottom.

b) Positioning the pipette tip a short distance above the bottom of the vessel.

These two modifications cause all of the pellet material to be within the region of maximum flow rate close to the pipette tip, so improving the resuspension efficiency.

Because this system requires only a single dimension of pipette movement (vertical) and visual feedback is unnecessary, automation of the necessary pipette actions is simple and reliable. Although the primary advantages of the system are seen in automated systems, the same system may be used manually.

Thus the invention provides in one aspect a magnetic separation method which comprises the steps of:

a) bringing a vessel having a bottom end and containing a liquid suspension of magnetically attractable particles into proximity with a magnet system whereby there is formed an annular or part-annular pellet comprising the magnetically attractable particles close to but not at the bottom end of the vessel, b) removing supernatant liquid from the vessel, and c) adding fresh liquid to the vessel, using the magnet system to draw the magnetically attractable particles to the bottom of the vessel, and resuspending the magnetically attractable particles in the fresh liquid.

In another aspect, the invention provides apparatus for performing the magnetic separation method which apparatus comprises an array of vessels each to contain a liquid suspension of magnetically attractable particles; a pipetting system for transferring liquid to and from the array of vessels; and a magnet system mounted for movement relative to the array of vessels, so as to be either free of the array of vessels or engaged with the array of vessels in one of two positions:

i) an annular separation position, ii) a pull-down separation position.

In yet another aspect, the invention provides a magnet system comprising: a carrier plate of non-magnetizable material; a back flow plate of magnetizable material overlying the carrier plate; a row of permanent magnets each positioned on the back flow plate with its N-S axis perpendicular to the back flow plate, the polarity of each permanent magnet being opposite to that of its neighbor or neighbors, the permanent magnets being spaced apart to define between them one or more work stations; a field concentrator plate of magnetizable material overlying the row of permanent magnets; and a cover plate of nonmagnetizable material overlying the field concentrator plate; there being provided a hole through the field concentrator plate and the overlying cover plate for locating a vessel at the work station.

An annular (or part-annular) pellet has the advantage that the particulate material is spread round the wall of the tube rather than up the wall. It is this feature as much as anything that enables the pellet to be positioned so low in the tube as to be immersed in a small volume of liquid added to the tube to re-suspend the particles.

An annular or part-annular pellet is one which is positioned on an internal side wall of the vessel (which is here presumed circular although this would not necessarily be so in practice) and extends all or part of the way round the side wall. As noted below, a part-annular pellet may comprise two portions generally on opposite sides of the vessel. Because the pellet is not at the bottom end of the vessel, a pipette can be inserted into the bottom end of the vessel in order to remove supernatant liquid without disturbing the pellet. Because the pellet is close to the bottom end of the vessel, it is immersed in the small volume of fresh liquid used to re-suspend the magnetically attractable particles.

The invention is applicable to round-bottom and conical-bottom vessels generally, of which microcentrifuge tubes (e.g. Eppendorf tubes and Sarstedt tubes) and microtitre plates are examples.

WO 91/12079 describes a method of recovering a biopolymer such as a nucleic acid from solution, by the use of magnetically attractable beads which do not specifically bind the polymer. The beads are suspended in the solution. Then the polymer is precipitated out of solution and becomes non-specifically associated with the beads by bead entrapment. When the beads are magnetically drawn down, the polymer is drawn down with them. After removal of supernatant liquid, fresh liquid can be added to the tubes to resolubilise the polymer and separate it from the beads.

Another standard system makes use of magnetically attractable beads which are coated with a reagent to specifically bind with the polymer to be recovered. The beads are added to a solution of the polymer. A magnet is used to pull the beads, with polymer bound to them, down into a pellet. The supernatant liquid is removed and fresh liquid added. The magnetizable beads are again drawn down. Then the fresh liquid is agitated to re-suspend the magnetizable beads and release into solution the polymer that was associated with them. Finally, the beads are again drawn down and removed.

The magnet system of this invention, involving an annular separation position and a pull-down separation position, is applicable to both these known techniques. The nature of the polymer and of the starting solution is not material to the invention, and a number of these can be listed by way of example:— a) Alcohol precipitation of nucleic acid molecules from solution;

b) Precipitation of bacteriophage and other viruses from solution;

c) Removal of bacterial DNA, proteins and membranes from bacterial lysates;

d) DNA preparation from bacteriophage or other viruses;

e) Precipitation of bacteria from solution.

The nature of the magnetically attractable particles is not material to the invention. Paramagnetic beads are commercially available and are suitable.

Preferred magnet systems involve permanent magnets, for example of Nd, Fe, B. Alternatively, electromagnet systems may be used. Electromagnet systems that are capable of forming the required fields have been designed and constructed. These multi-coil systems are designed to perform the annular and pull-down separation modes by switching between different coils.

Drawings Reference is directed to the accompanying drawings in which:—

FIG. 1 comprises sectional side elevations A and B of two conventional magnetic separation systems.

FIG. 2 comprises two parts A and B, each of which comprises two drawings. One is a side view and the other is a corresponding top view. FIG. 2A illustrates the annular separation step, and FIG. 2B illustrates the pull-down separation step of the present invention.

FIG. 3A comprises a side view and a corresponding top view of a magnet system for use in the invention.

FIG. 3B comprises a side view and a corresponding top view of another magnet system for use in the invention.

Figure 4A:
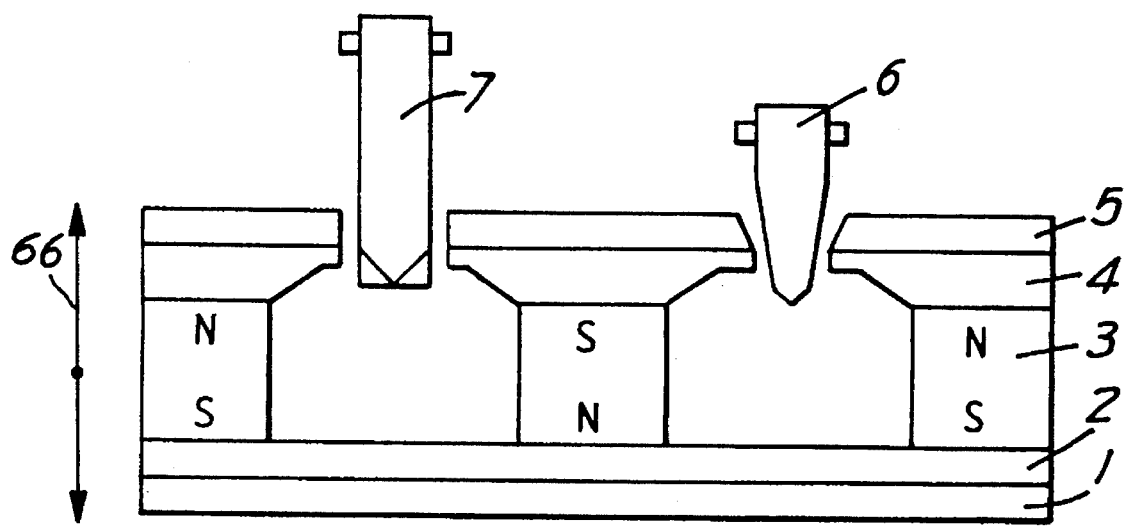
Figure 4B:
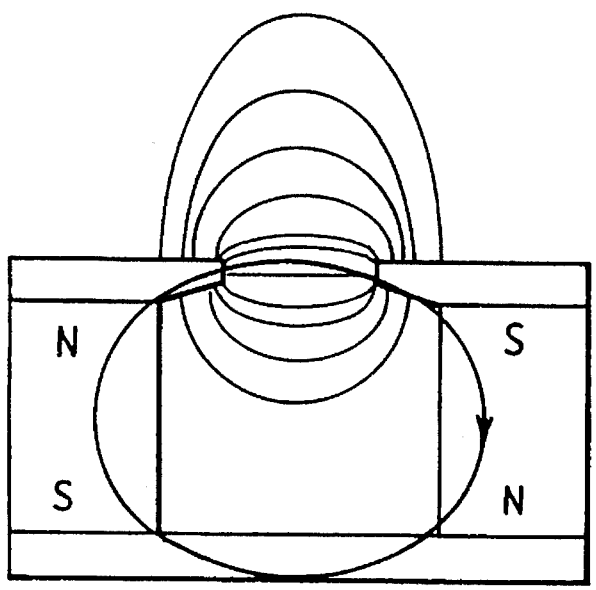

FIG. 4A is a side elevation of a preferred magnet system according to the invention, and FIG. 4B is an enlargement of part of FIG. 4a showing the magnetic field lines.

MAGNET SYSTEMS

The magnetic fields required to perform the annular and pull-down separations can be achieved in a number of ways, and some of these are described below.

In one embodiment, the magnet system is arranged with a N-S axis vertical or at least having a vertical component. Thus the magnet system may comprise a single magnet combined with an open-top cylindrical magnetic flux conductor. The bottom end of the vessel containing the liquid suspension of magnetically attractable particles is inserted into the open top of the cylindrical magnetic flux conductor in order to perform an annular pellet comprising the magnetically attractable particles.

Figure 2A:
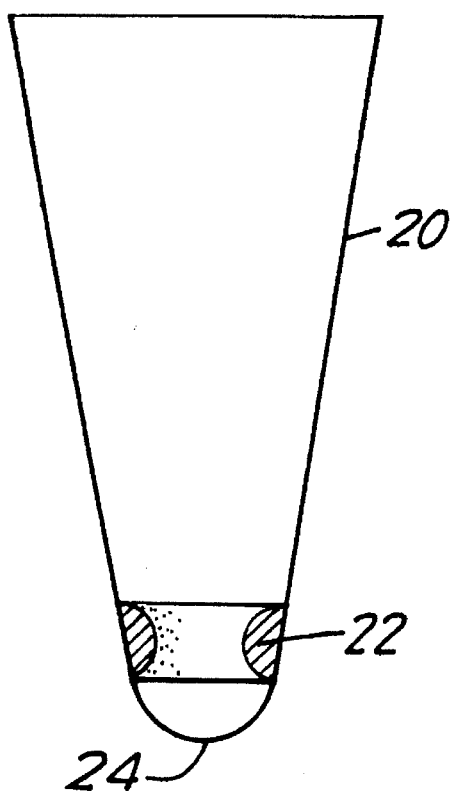
Figure 2A:
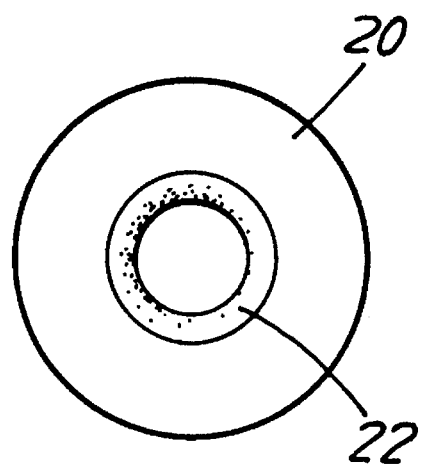
Figure 2B:
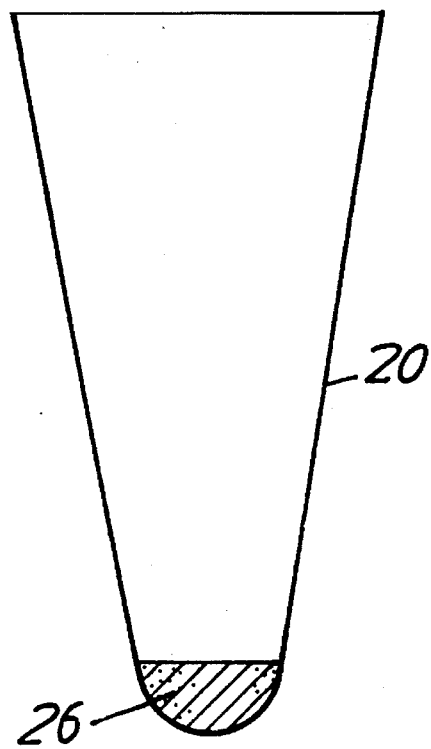
Figure 2B:
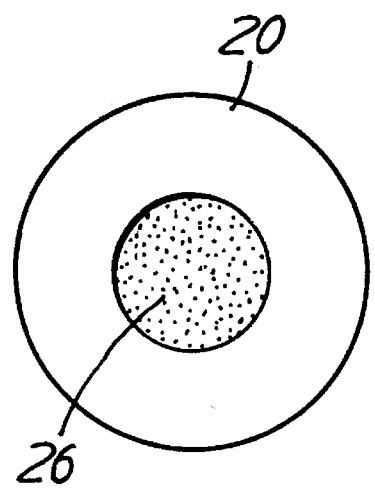

FIG. 3A comprises a side view and a corresponding top view of an embodiment of this system. The magnet system comprises a permanent magnet 30 of Neodymium/Iron/Boron, combined with an open-top cylindrical iron magnetic flux conductor 32. In use, a vessel containing a liquid suspension of magnetically attractable particles is lowered in the direction of the arrow 34 until its bottom end rests on/in the open top of the cylindrical magnetic flux conductor 32. There is a node of zero magnetic field along the vertical axis of the tube. By this means, an annular pellet is drawn down as shown in FIG. 2A. A pipette is inserted into the bottom end 24 of the tube, the supernatant liquid is removed, and the magnet is taken away. Then fresh liquid is introduced and the annular pellet resuspended in it. The pull-down separation (FIG. 2B) can conveniently be achieved by bringing the bottom end 24 of the vessel close to the flat surface 36 of the magnet. In an automated system it is likely to be more convenient to move the magnet system up underneath the vessel rather than to move the vessel itself.

Alternatively, the magnet system may generate a magnetic field gradient having a vertical component in a region into which the vessel containing the liquid suspension of magnetically attractable particles is brought in proximity with the magnet system. An embodiment is shown in FIG. 3B which comprises a side view and corresponding top view of the magnet system. This comprises a pair of permanent magnets 40, 42 on opposite sides of the position to be occupied by the vessel containing the liquid suspension. Each magnet is inclined with a lower pole facing an opposite lower pole of the other magnet. Thus for example, the N-S axis of the magnet 42 goes from 2 o'clock to 8 o'clock in the side view, and the N-S axis of the magnet 40 correspondingly goes from 10 o'clock to 4 o'clock. A lower magnetic flux conductor 44 overlies and is bonded to the lower side face of each magnet and serves both to conduct the field between the two magnets and to connect the two magnets together to form a rigid structure.

The upper side surface of each magnet 40, 42 carries an overlying upper magnetic flux conductor 46, 48. These two upper magnetic flux conductors define between them an opening 50 into which the bottom end of a vessel containing a liquid suspension of magnetically attractable particles is inserted, as shown by the arrow 52, in order to form part-annular pellets comprising the magnetically attractable particles.

The gradient field magnet system of FIG. 3B is somewhat more complex than the open field magnet system of FIG. 3A, but gives faster separation for a given mass of magnet.

A preferred magnet system is shown in FIGS. 4a and 4b. The magnet system comprises a carrier plate 1 of aluminum; a backflow plate 2 of iron overlying the carrier plate; a row of permanent magnets 3 of Nd, Fe, B; a field concentrator plate 4 of iron overlying the permanent magnets; and a cover plate 5 of aluminum overlying the field concentrator plate. Each permanent magnet is positioned on the back flow plate with its N-S axis perpendicular to the back flow plate, the polarity of each permanent magnet being opposite to that of its neighbor or neighbors. The permanent magnets are spaced apart at regular intervals to define between them work stations, of which two are shown in FIG. 4a. A hole is provided through the field concentrator plate and the overlying cover plate for locating a vessel at each work station. A Sarstedt tube 6 is shown in position at one work station, and an Elkay tube 7 in position at the other.

The field concentrator plate 4 has a flat upper surface and a tapered cross section. The plate is thicker where it overlies each magnet and thinner adjacent each work station. This tapered cross section creates a stray flux from magnetic north to south. Annular and pull-down separation positions are defined by the insertion depth of the vessel into the field concentrators. The intensity and the deep action of the stray field is mostly determined by the shape and material of the field concentrators. The other parameters affecting the magnetic field are the shape and material of the permanent magnets.

If the magnets are positioned in a single row, then the number of magnets is one more than the number of work stations, and each work station is affected by two magnets. Alternatively, the magnets may be arranged in an array with e.g. 4 or 6 magnets surrounding each work station. Means 66, are provided for movably mounting the magnet system relative to the array of vessels, so that the magnet system is either free of the array of vessels or engaged with the array of vessels in one of two positions: i) an annular separation position; ii) a pull-down separation position.

EXAMPLE 1

Two prototype instruments are working routinely in Applicant's laboratory to execute complete DNA preparation procedures using magnetic particles. These use an array of 48 permanent magnets with cylindrical flux conductors of the type shown in figure 3A. These are mounted on a motorized table which can move in the X and Z axes. This assembly is situated below a fixed 48 tube rack, above which is a robotic pipetting system which has movement in all three axes. The pipetting system consists of two syringe pumps connected to a needle mounted on the X/Y/Z robot via plastic tubing and a 'T' union. All systems are controlled form a single computer which enables complete procedures to be executed unattended.

Annular separation is achieved by moving the magnet table such that the base of each tube locates in the corresponding flux conductor. Moving the table to bring the base of the tube in contact with the upper surface of the magnet (to the left of the flux conductor in this case) produces the pull-down separation. The table can also be moved down sufficiently far that any field effect on the tubes is negligible.

The tube rack could potentially be moved to a fixed array of magnets instead, but this complicates the process of moving the pipetting needle to the tubes and so is not so suitable for an automated system.

EXAMPLE 2

The magnet system described in FIG. 4 has been used with two different kinds of tubes, both widely available commercially: Sarstedt 1.5 ml propylene tubes; and Elkay 5 ml propylene tubes. Polymer concentrations in solution in the vessels have ranged from 0.1 mg/ml to 5 mg/ml. Solvents have included water, ethanol, 70% ethanol in water, isopropanol, 20% polyethylene glycol in water, and neutralized *E. coli* lysates. Solution volumes have ranged from 20 to 1400 µl in Sarstedt tubes and from 100–5000 µl in Elkay tubes. The following protocols have been established:— a) For Elkay tubes containing 2–5 ml of solution. For annular separation, insert the tube 15 mm into the field concentrator; allow 90 seconds settling time; slow up movement to an insertion depth of 6 mm. The insertion depth is the distance from the bottom of the tube up to the top surface of the field concentrator plate. For pull-down separation, the protocol is: initial insertion depth 15 mm; settling time 90 seconds; slow up movement to an insertion depth of 1 mm.

b) Elkay tubes containing 100 µl to 2 ml solution. For annular separation, the insertion depth is 6 mm. For pull-down separation, the insertion depth is 1 mm. In each case a settling time of 90 seconds is allowed.

c) Sarstedt tubes. For annular separation the insertion depth is 4 mm. For pull-down separation, the insertion depth is 1 mm. Again, the settling time is 90 seconds.

We claim:

1. A magnet system comprising: a carrier plate of non-magnetizable material; a back flow plate of magnetizable material overlying the carrier plate; a row of permanent magnets each having opposed first and second ends, the first end of each said magnet being positioned on the back flow plate with a N-S axis oriented perpendicular to the back flow plate, the polarity of each permanent magnet being opposite to that of its neighbor or neighbor, the permanent magnets being spaced apart to define between them one or more work stations; a field concentrator plate of magnetizable material overlying said second ends of the permanent magnets; and a cover plate of nonmagnetizable material overlying the field concentrator plate; there being provided a hole through the field concentrator plate and the overlying cover plate for locating a vessel at the work station.

2. A magnetic separation method which comprises the steps of:

a) bringing a vessel having a bottom end and containing a liquid suspension of magnetically attractable particles into proximity with a magnet system whereby there is formed an annular or part-annular pellet comprising the magnetically attractable particles close to, but not at, the bottom end of the vessel;

b) removing supernatant liquid from the vessel; and c) adding fresh liquid to the vessel;

d) using the magnet system to draw the magnetically attractable particles to the bottom of the vessel;

e) removing the magnet system;

f) and re-suspending the magnetically attractable particles in the fresh liquid;

g) wherein the magnet system comprises a carrier plate of non-magnetizable material;

a back flow plate of magnetizable material overlying the carrier plate;

a row of permanent magnets each having opposed first and second ends, the first end of each said magnet being positioned on the back flow plate with a N-S axis oriented perpendicular to the back flow plate, the polarity of each permanent magnet being opposite to that of its neighbor or neighbors, the permanent magnets being spaced apart to define between them one or more work stations;

a field concentrator plate of magnetizable material overlying said second ends of the permanent magnets; and a cover plate of non-magnetizable material overlying the field concentrator plate;

there being provided a hole through the field concentrator plate and the overlying cover plate for locating a said vessel at the work station.

3. The method as claimed in claim 2, wherein during step c) sufficient fresh liquid is added to the vessel to submerge the annular or part-annular pellet.

4. The method as claimed in claim 2, wherein the vessel is a round-bottom or conical-bottom vessel.

5. A method of treating a solution of a polymer in a vessel having a bottom end, by the use of magnetically attractable particles which do not specifically bind the polymer, comprising the steps of:

a) suspending the magnetically attractable particles in the solution so as to form a liquid suspension of the magnetically attractable particles;

b) precipitating the polymer out of solution whereby it becomes non-specifically associated with the magnetically attractable particles;

c) bringing the vessel into proximity with a magnet system whereby there is formed an annular or part-annular pellet comprising the magnetically attractable particles and the precipitated polymer, said pellet being positioned close to, but not at, the bottom of the vessel;

d) removing a supernatant liquid from the vessel;

e) adding fresh liquid to the vessel;

f) using the magnet system to draw the magnetically attractable particles to the bottom of the vessel;

g) removing the magnet system;

h) redissolving the polymer in the fresh liquid; and k) wherein the magnet system comprises a carrier plate of non-magnetizable material;

a back flow plate of magnetizable material overlying the carrier plate;

a row of permanent magnets each having opposed first and second ends, the first end of each said magnet being positioned on the back flow plate with a N-S axis oriented perpendicular to the back flow plate, the polarity of each permanent magnet being opposite to that of its neighbor or neighbors, the permanent magnets being spaced apart to define between them one or more work stations;

a field concentrator plate of magnetizable material overlying said second ends of the permanent magnets; and a cover plate of non-magnetizable material overlying the field concentrator plate; there being provided a hole through the field concentrator plate and the overlying cover plate for locating a said vessel at the work station.

6. The method as claimed in claim 5, wherein the polymer is a nucleic acid.

7. The method as claimed in claim 5, wherein during step e) sufficient fresh liquid is added to the vessel to submerge the annular or part-annular pellet.

8. The method as claimed in claim 5, wherein the vessel is a round-bottom or conical-bottom vessel.

9. Apparatus which comprises:

an array of vessels each to contain a liquid suspension of magnetically attractable particles;

a pipetting system for transferring liquid to and from the array of vessels;

and a magnet system; and means for movably mounting the magnet system relative to the array of vessels, said means being adapted to bring the magnet system to any one of three positions and hold the magnet system in that position, the positions being:

i) engaged with the array of vessels in an annular separation position;

ii) engaged with the array of vessels in a pull-down separation position; and iii) free of the array of vessels; wherein the magnet system comprises:

a carrier plate of non-magnetizable material;

a back flow plate of magnetizable material overlying the carrier plate;

a row of permanent magnets each having opposed first and second ends, the first end of each said magnet being positioned on the back flow plate with a N-S axis oriented perpendicular to the back flow plate, the polarity of each permanent magnet being opposite to that of its neighbor or neighbors, the permanent magnets being spaced apart to define between them one or more work stations;

a field concentrator plate of magnetizable material overlying said second ends of the permanent magnets; and a cover plate of non-magnetizable material overlying the field concentrator plate; there being provided a hole through the field concentrator plate and the overlying cover plate for locating a said vessel at the work station.

\* \* \* \* \*